United States Patent [19]
Carloni et al.

[11] Patent Number: 5,849,952
[45] Date of Patent: Dec. 15, 1998

[54] UREA PRODUCTION PROCESS WITH HIGH ENERGY EFFICIENCY

[75] Inventors: Giuseppe Carloni; Franco Granelli, both of Milan, Italy

[73] Assignee: Shamprogetti S.p.A., Italy

[21] Appl. No.: 810,271

[22] Filed: Mar. 3, 1997

Related U.S. Application Data

[63] Continuation of Ser. No. 621,049, Mar. 22, 1996, abandoned, which is a continuation of Ser. No. 319,328, Oct. 6, 1994, abandoned, which is a continuation of Ser. No. 131,569, Oct. 4, 1993, abandoned, which is a continuation of Ser. No. 567,277, Aug. 14, 1990, abandoned.

[30] Foreign Application Priority Data

Feb. 19, 1992 [JP] Japan ..................................... 4-032308

[51] Int. Cl.$^6$ .................................................. C07C 273/04
[52] U.S. Cl. ................................ 564/71; 564/67; 564/68; 564/69; 564/70; 564/72
[58] Field of Search ................................. 564/67, 68, 69, 564/70, 71, 72

[56] References Cited

U.S. PATENT DOCUMENTS

| | | | |
|---|---|---|---|
| 3,356,723 | 12/1967 | Kaasenbrood | 564/66 |
| 3,711,454 | 1/1973 | Summerville | 564/71 |
| 4,296,252 | 10/1981 | Mavrovic | 564/70 |
| 4,354,040 | 10/1982 | Inoue et al. | 564/70 |
| 4,540,813 | 9/1985 | van Nassau et al. | 564/70 |
| 4,801,745 | 1/1989 | Meessen et al. | 564/70 |
| 4,801,746 | 1/1989 | Baenens | 564/70 |

FOREIGN PATENT DOCUMENTS

| | | |
|---|---|---|
| 0212744 | 3/1987 | European Pat. Off. . |
| 0266840 | 5/1988 | European Pat. Off. . |
| 1542371 | 3/1979 | United Kingdom . |

*Primary Examiner*—Shailendra Kumar
*Attorney, Agent, or Firm*—Rogers & Wells LLP; George P. Hoare

[57] ABSTRACT

A urea production process with high energy efficiency, in which the urea solution obtained from the synthesis stage is subjected to a first stage of high pressure thermal decomposition of the ammonium carbamate which has not undergone conversion to urea together with simultaneous self-stripping by excess ammonia, the gaseous products from said decomposition being condensed in two stages at different temperatures, in the first of which the heat is directly transferred to a second ammonium carbamate decomposition stage which is divided into two parts, namely a first thermal decomposition part and a second part consisting of adiabatic stripping with part of the carbon dioxide feed to the process.

1 Claim, 1 Drawing Sheet

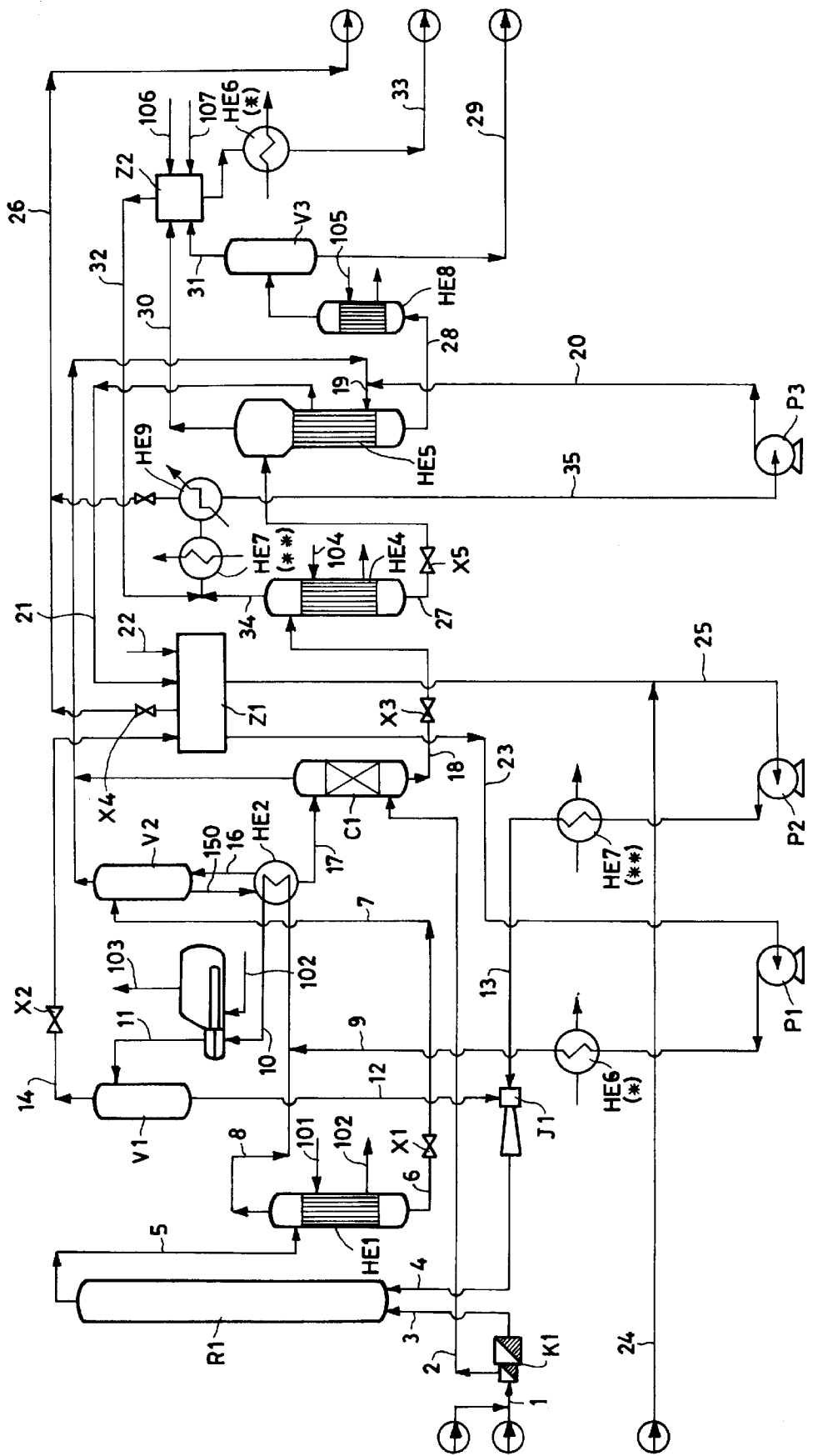

UREA PRODUCTION PROCESS WITH HIGH ENERGY EFFICIENCY

This application is a continuation of Ser. No. 08/621,049, filed Mar. 22, 1996, now abandoned; which application is a continuation of Ser. No. 08/319,328, filed Oct. 6, 1994, now abandoned; which application is a continuation of Ser. No. 08/131,569, filed Oct. 4, 1993, now abandoned; which application is a continuation of application Ser. No. 07/567,277 filed Aug. 14, 1990, (now abandoned).

BACKGROUND OF THE INVENTION

1. Field of the Invention

This invention relates to a process for producing urea by synthesis from ammonia and carbon dioxide which is highly energy-efficient, and in particular of very low heat consumption.

2. Description of the Prior Art

Urea is one of the chemical industry products most widely used in agriculture as a fertilizer and in the chemical industry itself as an intermediate, its production being considerable with the result that any reduction in its energy consumption is of considerable industrial importance.

The urea production process is based on the known synthesis from ammonia and carbon dioxide, in accordance with the following scheme.

The ammonia and carbon dioxide are fed into the synthesis section to form ammonium carbamate in accordance with the exothermic reaction:

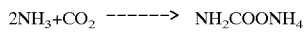
$$2NH_3 + CO_2 \longrightarrow NH_2COONH_4$$

A fraction of the ammonium carbamate then dehydrates to form urea and water in accordance with the endothermic reversible reaction:

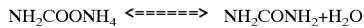
$$NH_2COONH_4 \rightleftharpoons NH_2CONH_2 + H_2O$$

Under the normally used synthesis conditions, i.e., pressures of between 120 and 300 bars and temperatures between 170° and 250° C., the carbamate formation reaction is extremely fast and practically complete, whereas the dehydration reaction proceeds slowly towards equilibrium.

That fraction of the ammonium carbamate which dehydrates to form urea is determined not only by the reaction temperature and pressure but also by the ratio of the various reactants and the residence time in the synthesis section.

The molar ratios normally used are:
ammonia/carbon dioxide: from 2.5 to 7
water/carbon dioxide: from 0 to 1.

Water is present both as reaction product and a component of any recycle streams from the plant sections downstream of the synthesis section.

The residence time in the synthesis section varies from 20 to 90 minutes.

The product of the synthesis reaction consists substantially of a solution comprising ammonium carbamate, urea, water and free ammonia, in that all the industrially used processes operate with a substantial excess of ammonia to obtain high yields and limit the formation of harmful by-products such as biuret. The free ammonia and the ammonium carbamate are separated from the urea solution obtained from the synthesis section and recycled to the synthesis section for their complete conversion into urea. The urea solution then has to be further processed to obtain the granular product in accordance with current commercial specifications. The various industrial urea production processes are characterised precisely by their methods for separating and recycling those components not converted to urea.

To better illustrate the technical problems involved in the present invention, a description will now be given of a known urea production process.

The overall urea production process is divided into the following main stages, as described in GB patent No. 1,542,371 of the present applicant and representing one successful embodiment thereof, starting from ammonia and carbon dioxide:

a) feeding the urea synthesis reactor, operating at high pressure, with carbon dioxide and an excess of ammonia over the stoichiometric amount, to obtain an aqueous solution of urea, ammonium carbamate and free ammonia;

b) feeding said solution to a high pressure decomposer at substantially the same pressure as the synthesis reactor, and decomposing that fraction of the carbamate contained in said solution to ammonia and carbon dioxide as is determined by the thermodynamic equilibrium established under the prevailing temperature and pressure conditions of the urea solution, and supplying the heat necessary to sustain the decomposition reaction;

c) at high pressure still substantially equal to that of stage a), condensing in a condenser the decomposition products of stage b), i.e., ammonia and carbon dioxide which are produced in the gaseous phase, to recover the heat of condensation of said gaseous products;

d) recycling the condensate from stage c) to the synthesis stage a);

e) feeding the urea solution obtained from the high pressure decomposer of stage b) and still containing a considerable quantity of ammonium carbamate and dissolved ammonia, to a medium pressure decomposer operating at much lower pressure, of the order of 20 bars, in which further decomposition is effected to obtain a purer urea solution plus further gaseous products; the decomposition reaction of said second decomposition stage is also sustained by supplying the necessary heat;

f) transferring the gaseous products obtained from the medium pressure decomposer to a condenser at the same pressure, in which they are condensed;

g) separating the condensate from stage f) into a first liquid phase comprising the ammonium carbamate and a second liquid phase consisting of substantially pure ammonia;

h) recycling the first liquid phase comprising the ammonium carbamate to the high pressure condenser;

i) recycling the second liquid phase consisting of substantially pure ammonia to the synthesis reactor;

j) transferring the urea solution from the medium pressure decomposer of stage e) to a low pressure decomposer operating at a pressure of the order of 4 bars; to produce as overhead product a vapor stream consisting of ammonia, carbon dioxide and water, and a bottom product consisting of a urea solution still containing a small quantity of ammonia and carbon dioxide;

k) condensing the overhead vapor stream of the preceding stage in a low pressure condenser;

l) concentrating the aqueous urea solution from the low pressure decomposer in a vacuum concentration section, in one or more stages, to obtain molten urea and a vapor stream consisting essentially of water with a small quantity of ammonia, carbon dioxide and urea;

m) condensing the vapor stream of water, ammonia and carbon dioxide from stage 1);

n) treating the condensate from stage m) to purify the effluent, hydrolyzing the urea and recovering the ammonia and carbon dioxide.

The high pressure carbamate decomposition stage b) comprises thermal decomposition to ammonia and carbon dioxide, with simultaneous self-stripping by the excess ammonia as in GB Patent No. 1,184,004 of the present applicant, and is typically implemented in a falling film heat exchanger as in GB Patent No. 1,552,682 of the present applicant.

Stage c) i.e., the condensation of the vapor stream from the high pressure decomposer, consisting of ammonia, carbon dioxide and water, represents a fundamental stage of the process from the energy viewpoint. The heat involved in this stage is considerable and is generally used to produce low pressure steam, as for example in U.S. Pat. No. 3,356,723 in the name of Stamicarbon, and is used as a heat source for sustaining the low pressure decomposition reaction of stage j), for concentrating the urea solution of stage l) and in the effluent purification section of stage n).

However, the temperature level of the steam produced in the high pressure condenser is not sufficient for feeding the medium pressure decomposition stage e) for which a temperature exceeding 160° C. is required, and for this stage a heating medium at a temperature exceeding that of the available steam from the high pressure condenser has to be provided, with considerable negative effect on the process energy balance.

The condensation stage f) for the vapor stream produced by the medium pressure decomposer represents another of the points of major thermal inefficiency of the process. The urea solution produced in the high pressure decomposition stage b) contains not only residual ammonium carbamate, urea and water but also a considerable quantity of free ammonia with the result that the vapor stream generated in the medium pressure decomposition stage e) is richer in ammonia than the stoichiometric 2:1 ratio required by the carbamate. This high molar ratio of ammonia to carbon dioxide negatively influences the temperature at which the heat of condensation of the product vapor stream of stage e) is available in the medium pressure condenser of stage f), and cannot be effectively recovered in the plant, to the consequent disadvantage of the energy balance.

A further point of thermal inefficiency of the described process involves the condensation in stage k) of the vapor phase obtained from the low pressure decomposition stage j). Again in this condensation, the high ammonia/carbon dioxide ratio negatively influences the condensation temperature, and the relative heat of condensation cannot be usefully recovered. In addition to this, complete absorption of the free ammonia requires a considerable quantity of water, which has finally to be recycled to the synthesis section where it negatively influences the conversion of the carbamate into urea and the plant energy efficiency.

The technical problem caused by the aforesaid stages of low energy efficiency is solved according to the present invention by raising the temperature level at which the heat is recovered on condensing the vapor streams produced in the carbamate decomposition stages so that this heat can be more effectively used in the process. For better use of the low pressure steam produced in the condensation stage c) for the product gaseous phase of stage b) it has been proposed in the literature to raise its level by compressors or boosters to enable it to be used in the medium pressure decomposition stage e). This solution complicates the plant and requires additional electricity or high or medium pressure steam consumption, with questionable advantages to the overall energy balance.

It has also been proposed to directly transfer the high pressure condensation heat to the medium pressure decomposer. In European Patent Application No. 212,744 in the name of Stamicarbon this direct transfer is implemented by a process in which the high pressure condensing vapor stream and the urea solution transferred to the medium pressure decomposer originate from a first decomposition stage with simultaneous stripping with carbon dioxide. The use of stripping with carbon dioxide means that the ammonia/carbon dioxide ratio in stage a) has to be limited, thereby limiting the conversion of carbamate to urea.

In the described process, the vapor stream does not have a composition such as to enable the heat of condensation to be made available at a temperature sufficiently high for use in the medium pressure decomposer.

To attain this, it is necessary to use a large-volume high pressure condenser known as a pool condenser, which is sized to give a residence time sufficient for a considerable fraction of the condensed carbamate, for example 30% of the equilibrium quantity, to be converted to urea. The high pressure condenser thus becomes a synthesis pre-reactor. This modification is very costly in terms both of investment and installation. U.S. Pat. No. 4,354,040 in the name of Toyo Eng. Corp. implements this direct heat transfer in a process analogous to that of European Patent Application No. 212,744 but with a higher ammonia/carbon dioxide ratio. This requires a higher operating pressure in all the high pressure sections, i.e., synthesis reactor, decomposer and condenser, with a reduction in the efficiency of the decomposer and increased energy consumption for compressing the carbon dioxide and for recycling the unconverted reactants from the lower pressure section. In any event, the medium pressure decomposition of the ammonium carbamate is unsatisfactory and make-up heat has to be supplied from the outside, such as in the form of high or medium pressure steam, to sustain the medium pressure decomposition.

The processes of the cited patents EP-212,744 and U.S. Pat. No. 4,354,040 are characterised by a high pressure decomposition stage with simultaneous stripping with carbon dioxide, producing an ammonium carbamate solution with a very low free ammonia content, so that the released vapor stream has an ammonia/carbon dioxide ratio adequate for effective use of the medium pressure condensation heat.

In contrast, in those processes comprising a high pressure decomposition stage with simultaneous self-stripping with the free ammonia contained in the effluent of the synthesis reactor, the molar ammonia/carbon dioxide ratio in the vapor stream to be condensed in the medium and low pressure condensation stages is unfavorable both for effective use of the heat developed during condensation and because of the quantity of water or other aqueous solvents which have to be introduced into the cycle for its complete condensation.

Various process modifications have been proposed to improve the low pressure condensation conditions.

U.S. Pat. No. 4,354,040 proposes to feed part of the carbon dioxide directly into the low pressure decomposition stage to obtain a better level of condensation temperature by adjustment of the $NH_3/CO_2$ ratio.

However the relative heat of condensation, released in the low pressure condenser, is not completely usable, to the disadvantage of the thermal efficiency of the process.

Said European Patent Application No. 212,744 proposes to subject the urea solution from the medium pressure decomposition stage to additional stripping with the vapor stream originating from a preceding adiabatic expansion stage, i.e., "flash", carried out on the urea solution from the high pressure decomposition stage.

This stripping action enables the low pressure decomposition stage be fed with a urea solution of low free ammonia content, and the quantity of water or aqueous solvents required for completing the low pressure condensation limited. This arrangement is, however not completely satisfactory because of the presence of significant quantities of ammonia in the vapor phase used in the stripping.

SUMMARY OF THE INVENTION

The present invention obviates the drawbacks of the aforesaid processes by allowing more efficient use of the heat obtained in condensing the vapor streams from the various decomposition stages within the process itself. The process according to the present invention comprises a medium pressure decomposition stage for the ammonium carbamate in which the heat required for said decomposition is provided directly by the condensation of the vapor stream produced by the high pressure decomposition without the need for additional high temperature sources, and a stage in which the urea solution produced by the medium pressure decomposition stage is subjected to adiabatic stripping with part of the feed carbon dioxide, to provide a double beneficial effect, namely a more favorable $NH_3/CO_2$ ratio in the medium pressure condensation stage and the availability for feed to the low pressure section of a urea solution substantially free of free ammonia, to generate in said low pressure section a vapor stream which can be condensed completely with little water addition, so also improving the reaction efficiency.

BRIEF DESCRIPTION OF THE DRAWING

The drawing is a flow diagram illustrating the urea production process according to the present invention.

DESCRIPTION OF PREFERRED EMBODIMENTS

The present invention provides a urea production process comprising the following main stages. The flow diagram of the drawing, which relates to the example given hereinafter, can be referred to for a better understanding of the flow scheme.

A) The synthesis stage is conducted at a temperature of 175°–195° C., and preferably 180°–195° C., and a corresponding pressure of 130–220 bars, and preferably 140–180 bars, with a feed consisting of ammonia, carbon dioxide containing inerts and passivating air (known overall as noncondensables hereinafter) and unconverted recycle ammonium carbamate, maintaining in the synthesis reactor a molar $NH_3/CO_2$ ratio of between 3.0 and 5.0, and preferably between 3.2 and 3.7.

B) The synthesis product, consisting of an aqueous solution of urea, carbamate and free ammonia, is transferred to a high pressure decomposition stage consisting of a falling film heat exchanger and operating substantially at the same pressure as the synthesis. Thermal decomposition of the ammonium carbamate takes place in this heat exchanger, with simultaneous self-stripping of the free ammonia.

C) The gaseous phase obtained from stage B) and consisting of ammonia, carbon dioxide and water is transferred to condensation in the medium pressure decomposition stage.

D) The urea solution leaving the high pressure decomposition stage is fed to a medium pressure section operating at 10–30 bars, and preferably 13–25 bars, where after separating the flash vapor the urea solution is transferred to a medium pressure decomposition stage in which thermal decomposition of the carbamate still contained in said solution takes place by direct transfer of the heat released by the partial high pressure condensation of the vapor stream from the previous stage C).

E) The ammonium carbamate solution and the vapor uncondensed during the condensation of stage D) are transferred to a further high pressure condensation stage in which recovery of the heat available in the high pressure vapor is completed. In this stage the heat is recovered to produce low pressure steam, preferably at 4–7 bars, for use in other section of the plant. The noncondensables are separated and the ammonium carbamate solution is recycled to synthesis by a liquid-liquid ejector using the feed ammonia as drive fluid.

F) The urea solution leaving the medium pressure decomposition stage is used in an adiabatic stripping stage substantially at the same pressure as the medium pressure decomposition stage, and in which after separating the gas produced by the ammonium carbamate decomposition, the solution of urea, residual carbamate and free ammonia is brought into countercurrent contact with gaseous carbon dioxide. For this treatment a fraction of the feed carbon dioxide is used, this fraction being between 3% and 20%, and preferably between 5% and 15%, of the feed carbon dioxide. This treatment results in an aqueous urea solution containing a small quantity of free ammonia, and with a molar $NH_3/CO_2$ ratio of 2.2–4.0 and preferably 2.5–3.5.

G) Transferring the gaseous phase obtained from the medium pressure decomposition stage and the gaseous phase obtained from the medium pressure adiabatic stripping with carbon dioxide to the urea solution vacuum preconcentration stage to recover the heat of condensation of said gaseous streams.

H) Transferring the urea and ammonium carbamate solution from the medium pressure stripping stage F) to a low pressure decomposition stage operating at a pressure of about 4 bars, and consisting of a falling film heat exchanger in which the ammonium carbamate still present in the solution is further decomposed to obtain as bottom product a urea solution containing residual quantities of ammonia and carbon dioxide.

I) Transferring the urea solution obtained in stage H) to the vacuum preconcentration stage where, in a falling film heat exchanger operating at a pressure of 0.3–0.95 bars abs. and preferably 0.35–0.5 bars abs, the solution is preconcentrated to a urea concentration of 80–95% by weight and preferably 85–94% by weight, by direct transfer of the heat released by the partial condensation of the vapor stream from stage G).

L) Feeding the preconcentrated urea solution to a final concentration stage and solidifying it by prilling in a tower to produce prilled urea or granulating it to produce granulated urea.

M) Condensing the vapor streams produced in the concentration stages I) and L), treating the condensate to obtain a practically pure effluent, and recycling the ammonia and carbon dioxide to the low pressure condensation stage.

N) Low pressure condensation of the vapor streams obtained from stages H) and M) in a condensation stage operating substantially at the same pressure as the low pressure decomposition stage, the heat of condensation being used to preheat the ammonia feed to the high pressure synthesis section and the condensate obtained being recycled to stage I) on the condensing vapor side.

O) Transferring the ammonium carbamate solution and the vapor resulting from the partial condensation on the shell side of the film heat exchanger of stage I) to a condensation/separation stage in which a first liquid phase containing ammonium carbamate and a second liquid phase containing substantially pure ammonia are produced.

P) recycling the first phase containing ammonium carbamate to the high pressure vapor condensation regions D) and E).

Q) Mixing the second liquid phase consisting of practically pure ammonia with the plant feed ammonia, preheating the total ammonia in the preceding low pressure condensation stage N) and feeding it to the high pressure synthesis section A) through a liquid/liquid ejector for recycling the ammonium carbamate, in which the liquid ammonia acts as the drive fluid.

Stages C), D), F), G), I) and N) form the characterising part of the process according to the invention.

Compared with the processes of the known art, the process according to the invention advantageously reuses the heat of condensation of the vapor streams produced in the various carbamate decomposition stages within the process itself, so considerably reducing the amount of external heat to be supplied.

The following advantages are particularly important:

the heat released in the high pressure condensation stage is used in the medium pressure decomposition stage without the need for additional external high temperature heat;

the heat released in the medium pressure condensation stage is effectively used in the vacuum concentration of the urea solution in a falling film apparatus, enabling a concentrated urea solution of up to 90–95% by weight to be obtained from this stage;

the low pressure condensation stage is effected with minimum addition of absorption water, with improved conversion of ammonium carbamate to urea, and at a temperature still sufficiently high to preheat the feed ammonia.

The characteristics and advantages of the present invention will be more apparent from following example, which illustrates a typical embodiment thereof with reference to the flow diagram of the Figure.

EXAMPLE

A plant in accordance with the flow diagram of the drawing was used to produce 300 tonnes/day of urea, equivalent to 12500 kg/h. 9167 kg/h of carbon dioxide, 21 kg/h of inerts and 61 kg/h of air as passivation agent are fed through the line 1 to the suction side of the compressor K1 and hence to the plant. 910 kg/h with 8 kg/h of associated inerts are taken from an intermediate stage of K1 at a pressure of 17 bars and at a temperature of 220° C., and fed through the line 2 to the adiabatic stripping column C1. The remaining 8257 kg/h of carbon dioxide and 74 kg/h of inerts are fed to the synthesis reactor R1 through the line 3 at 120° C. and 155 bars.

A mixture of ammonia and ammonium carbamate comprising 18970 kg/h of ammonia, 6184 kg/h of carbon dioxide and 2954 kg/h of water is also fed to the reactor R1 through the line 4.

After a residence time of 30 minutes, the reaction mixture leaving the reactor R1 at a temperature of 190° C. and pressure of 150 bars consists of 11717 kg/h of ammonia, 5054 kg/h of carbon dioxide, 12800 kg/h of urea, 6794 kg/h of water and 74 kg/h of noncondensables. It is fed through the line 5 to the falling film decomposition stage HE1 operating substantially at the same pressure as the reactor R1.

5875 kg/h of saturated steam at a pressure of 22 bars are fed through line 101 to the shell side of the decomposition stage HE1 and condensed. The condensate obtained is fed to the shell side of the carbamate condenser HE3 through the line 102 to generate further steam, this time at low pressure.

From the bottom of the decomposition stage HE1 a urea solution at a temperature of 202° C. is obtained containing 7588 kg/h of ammonia, 2582 kg/h of carbon dioxide, 12560 kg/h of urea and 6286 kg/h of water, and is fed through the line 6 to the expansion valve X1 where the pressure is reduced from 150 bars to 17 bars. The resultant mixture is then fed through the line 7 to the separator V2 where the flash vapor is released, the bottom urea solution being fed through the line 15 to the medium pressure decomposition stage HE2.

The vapor stream from the top of the high pressure decomposition stage HE1 consists of 4265 kg/h of ammonia, 2648 kg/h of carbon dioxide, 436 kg/h of water and 74 kg/h of noncondensables, at a pressure of 150 bars and temperature of 190° C., and after mixing with the recycle ammonium carbamate solution is fed to the medium pressure decomposition stage HE2 through the line 8, to provide the heat required for the medium pressure decomposition. The recycle ammonium carbamate, consisting of 4427 kg/h of ammonia, 536 kg/h of carbon dioxide and 2518 kg/h of water, is fed through the line 9. This stream is very useful for supplying water which enables the condensation to be conducted with maximum heat recovery, and can also be varied by dividing it between the upstream and downstream sides of the heat exchanger HE2. The high pressure vapor is partly condensed in the medium pressure decomposition stage HE2 and the liquid/vapor leaving at a temperature of 170° C. is fed to the ammonium carbamate condenser HE3, consisting preferably of a horizontal kettle-type reboiler, where the still available heat of condensation is used to produce 4925 kg/h of steam at a temperature of 147° C. and pressure of 4.4 bars, which is fed to the low pressure steam manifold through the line 103.

The mixture of condensed ammonium carbamate and noncondensables at 155° C. leaving the carbamate condenser HE3 is fed through the line 11 to the separator V1 where a liquid phase separates consisting of 7767 kg/h of ammonia, 6184 kg/h of carbon dioxide and 2954 kg/h of water, and is fed through the line 12 to the suction side of the liquid/liquid ejector J1, which uses 112 03 kvh of ammonia as drive fluid fed at 200 bars and 100° C. through the line 13. The resultant mixture is then fed to the synthesis reactor through the line 4.

The vapor phase released from the top of the separator V1, consisting of 925 kg/h of ammonia and 74 kg/h of noncondensables, is fed through the line 14 and expansion valve X2 to the ammonia condensation/separation zone Z1. The urea solution leaving the separator V2 is fed through the line 15 to the medium pressure decomposition stage HE2 where it decomposes to provide as top product a vapor phase which is recycled to the separator V2 through the line 16, and as bottom product a urea solution at a temperature of 155° C. consisting of 1344 kg/h of ammonia, 536 kg/h of carbon dioxide, 12560 kg/h of urea and 5269 kg/h of water, which is fed through the line 17 to the adiabatic stripping column C1 where it is brought into intimate countercurrent contact with the carbon dioxide withdrawn from the intermediate stage of the compressor K1 and fed through the line 2.

The bottom product from the stripping stage is a urea solution at a temperature of 147° C. consisting of 803 kg/h of ammonia, 669 kg/h of carbon dioxide, 12560 kg/h of urea and 5085 kg/h of water, with a molar $NH_3/CO_2$ ratio of 3.1.

This solution is then fed through the line 18 and expansion valve X3 to the low pressure falling film decomposition stage HE4 operating at 4 bars.

The vapor streams obtained from the top of the separator V2 and adiabatic stripping column Cl, and consisting of 6785 kg/h of ammonia, 2823 kg/h of carbon dioxide, 1201 kg/h of water and 8 kg/h of noncondensables, are combined and after mixing with the low pressure recycle ammonium carbamate are fed to the shell side of the preconcentrator HE5 through the line 19. The recycle ammonium carbamate consists of 837 kg/h of ammonia, 713 kg/h of carbon dioxide and 917 kg/h of water, has a temperature of 55° C. and is fed through the line 20.

The low pressure vapor is partly condensed in the heat exchanger HE5 and the resultant liquid/vapor mixture consisting of an ammonium carbamate solution and ammonia vapor at a temperature of 110° C. is recycled to the ammonia condensation/separation zone Z1 through the line 21.

The ammonia condensation/separation zone Z1 is analogous to that already fully described in terms of configuration and operation in the said GB Patent No. 1,542,371 of the present applicant. 400 kg/h of water are also fed to the section Z1 through the line 22. This water is used to wash the inerts and completely remove the ammonia contained in them.

The following are obtained from the separation/condensation zone Z1:

an ammonium carbamate solution at a temperature of 85° C. consisting of 4427 kg/h of ammonia, 3536 kg/h of carbon dioxide and 2518 kg/h of water, which is fed through line 23 to the suction side of the high pressure ammonium carbamate pump P1. The ammonium carbamate solution is then recycled to the high pressure condensation section through the line 9 after being preheated to 120° C. by the process condensate from the section Z2 in the heat exchanger HE6 which implements the heat transfer between the fluids of the lines 33 and 9. For flow diagram simplicity, the heat exchanger HE6 is shown twice in the drawing once in the line 9 and once in the line 33, but is in fact the same unit;

a stream consisting of 4120 kg/h of recycle liquid ammonia which is combined with the 7083 kg/h of fresh ammonia fed to the plant through the line 24; the total of 11203 kg/h of ammonia is fed through the line 25 to the suction side of the high pressure ammonia pump P2. The ammonia is pumped to 200 bars and is then preheated in the heat exchanger HE7 to a temperature of 100° C. and fed through the line 13 to the reaction section in which, before being used for the synthesis, it is used as the drive fluid to the ejector J1. The ammonia is preheated using the heat of condensation of the vapor stream in the low pressure condensation section.

As in the case of the heat exchanger HE6, there is only one heat exchanger HE7 but this is shown twice in the flow diagram, in each of the fluid lines concerned, to simplify the drawing of these lines;

a stream consisting of 82 kg/h of noncondensables which are bled from the plant through the line 26 and the pressure control valve X4.

The low pressure film decomposition stage HE4 is fed with 1150 kg/h of low pressure steam through the line 104, to produce a further decomposition of the residual ammonium carbamate and obtain as bottom product a urea solution consisting of 245 kg/h of ammonia, 70 kg/h of carbon dioxide, 12560 kg/h of urea and 4594 kg/h of water at a temperature of 138° C. This solution is fed through the line 27 and expansion valve X5 to the film preconcentrator HE5 operating at a pressure of 0.35 bars abs. where, by the partial condensation of the medium pressure vapor stream fed through the line 19, the urea solution is concentrated to 90.1% by weight. The urea solution is fed from the preconcentrator HE5 through the line 28 to the final concentrator HE8 and to the separator V3 where a stream of molten urea consisting of 12560 kg/h of urea and 25 kg/h of water is separated and fed to the final finishing stage for granulation or prilling.

The final stage requires 1825 kg/h of low pressure steam, which is fed through the line 105.

The vapor streams produced in these final stages, i.e., in HE5 and in HE8/V3, are fed through the lines 30 and 31 to the condensation/treatment effluent zone Z2 to which 1950 kg/h of low pressure stream are fed through the line 106 for the vacuum extraction of vapor and for stripping the ammonia and carbon dioxide contained in the process condensate. Through the line 107, 250 kg/h of high pressure steam are also fed to the section Z2 for the complete hydrolysis of the urea entrained by the vapor in the preconcentration section HE5 and in the final concentration section HE8/V3.

The final treatment zone Z2 is analogous to that already fully described in terms of configuration and operation in the said GB Patent No. 1,542,371 of the present applicant.

The following streams are obtained from the section Z2:

a gaseous stream composed of 279 kg/h of ammonia, 114 kg/h of carbon dioxide and 426 kg/h of water, which is recycled through the line 32 to the low pressure condensation section;

a liquid stream consisting of 6325 kg/h of purified water at a temperature of 139° C. which is expelled from the plant through the line 33 after its sensible heat has been recovered in the heat exchanger HE6 for preheating the ammonium carbamate recycled to the high pressure condensation section.

The recycle vapor stream from the zone Z2, recycled through the line 32, is mixed with the vapor leaving the top of HE4 through the line 34 and is then fed to the low pressure ammonium carbamate condensers HE7 and HE9.

In the condenser HE7 part of the heat of condensation is used to preheat the high pressure ammonia fed to the high pressure section through the line 13. In the condenser HE9, the vapor is completely condensed at a temperature of 55° C. and the heat of condensation is removed by cooling water.

The ammonium carbamate solution leaving the condenser HE9 consists of 837 kg/h of ammonia, 713 kg/h of carbon dioxide and 917 kg/h of water and is fed through the line 35 to the suction side of the pump P3, which recycles the ammonium carbamate solution to the medium pressure condensation stage through the line 20. The low pressure steam requirements of the final process sections are satisfied by the low pressure steam production obtained from the condenser HE3.

The described embodiment is very low in energy consumption and, including the treatment of the produced effluents, the specific utilities consumptions per tonne of product urea are:

medium pressure steam: 470 kg/t
high pressure steam: 20 kg/t
electricity: 20 kwh/t*
cooling water: 60 m³/t**

NB:
* not including $CO_2$ compression
** temperature 10° C.

We claim:

1. In a process for producing urea from ammonia and carbon dioxide having a synthetic step yielding a gaseous phase consisting of urea, carbamate ammonia, and water, wherein the process has a high pressure decomposition stage yielding an aqueous urea solution having carbamate contained therein, and a medium pressure decomposition stage operating at 10–30 bars, wherein the urea solution is fed from the high pressure decomposition stage to the medium pressure decomposition stage after flash vapor is separated therefrom, wherein the carbamate is thermally decomposed by direct transfer of heat released by the condensation of the vapor, wherein the process also has an adiabatic stripping stage for receiving the urea solution from the medium pressure decomposition stage, wherein the adiabatic stripping stage is substantially at the same pressure as the medium pressure decomposition stage, wherein after separating gas produced by the decomposition of the carbamate, the urea solution, residual carbamate, and free ammonia, the urea solution is brought into counter-current contact with a fraction of the carbon dioxide, wherein the fraction is about 3% to about 20%, wherein the process also has a vacuum preconcentration stage for recovering the heat of condensation from gaseous streams and a first transferring stage for transferring gas from the medium pressure decomposition stage and the adiabatic stripping stage to the vacuum preconcentration stage, wherein the process further has a second transferring stage for transferring the urea solution to the vacuum preconcentration stage, wherein the vacuum preconcentration stage has a heat exchanger operating at a pressure of about 0.3 bars to about 0.95 bars, and wherein the urea solution is preconcentrated to about 80% to about 95% by weight by direct transfer of the heat released by the partial condensation of the vapor, and wherein the process still further has a condensation stage and a low pressure decomposition stage each operating at substantially the same pressure for low pressure condensation of the vapor stream, and wherein the heat of condensation is for preheating the ammonia, the process comprising:

(a) reacting in a synthesis reactor the ammonia and the carbon dioxide containing inerts and passivating air (hereinafter known collectively as noncondensables), and unconverted recycled ammonium carbamate at a temperature of 175° C.–195° C., and a corresponding pressure of 130–220 bars, while maintaining in the synthesis reactor a molar $NH_3/CO_2$ ratio of between 3.0 and 5.0;

(b) transferring the product from step (a), essentially consisting of an aqueous solution of urea, carbamate and free ammonia, to the high pressure decomposition stage essentially consisting of a falling film heat exchanger and operating substantially at the same pressure as in step (a), to produce a gaseous phase and an aqueous urea solution;

(c) transferring the gaseous phase obtained from step (b), essentially consisting of ammonia, carbon dioxide, and water to condensation in the medium pressure decomposition stage;

(d) transferring the aqueous urea solution from step (b) to the medium pressure decomposition stage;

(e) transferring the ammonium carbamate solution and uncondensed vapor resulting from step (d) to a further high pressure condensation stage in which recovery of the heat available in the high pressure vapor is completed, wherein in this stage heat is recovered to produce low pressure steam, noncondensables are separated, and ammonium carbamate solution is recycled to step (a) by a liquid-liquid ejector using the feed ammonia as drive fluid;

(f) feeding the urea solution leaving the medium pressure decomposition stage to the adiabatic stripping stage resulting in an aqueous urea solution containing a small quantity of free ammonia, and wherein the molar $NH_3/CO_2$ ratio is 2.2–4.0;

(g) transferring the gaseous phase obtained from the medium pressure decomposition stage and the gaseous phase obtained from the medium pressure adiabatic stripping to a urea solution vacuum preconcentration stage to recover the heat of condensation of said gaseous streams;

(h) transferring the urea and ammonium carbamate solution from step (f) to the low pressure decomposition stage which operates at a pressure of about 4 bars, and which essentially consists of a falling film heat exchanger in which the ammonium carbamate still present in the solution is further decomposed to obtain as a bottom product a urea solution containing residual quantities of ammonia and carbon dioxide;

(i) transferring the urea solution obtained in step (h) to the vacuum preconcentration stage wherein a vapor stream is produced;

(j) feeding the preconcentrated urea solution from step (i) to a final concentration stage and solidifying the urea therein either by prilling it in a tower to produce prilled urea or granulating it to produce granulated urea, thereby also producing a vapor stream;

(k) condensing the vapor streams produced in the concentration steps (i) and (j), treating the resulting condensate to obtain a practically pure effluent, and recycling the ammonia and carbon dioxide to a low pressure condensation stage;

(l) condensing, at low pressure, the vapor streams obtained from steps (h) and (k) in a condensation stage operating substantially at the same pressure as the low pressure decomposition stage of step (h), the heat of condensation being used to preheat the ammonia feed in step (a) and the condensate obtained being recycled to step (i) on the condensing vapor side;

(m) transferring the ammonium carbamate solution and the vapor resulting from the partial condensation on the shell side of the film heat exchanger of step (i) to a condensation/separation stage wherein a first liquid phase containing ammonium carbamate and a second liquid phase containing substantially pure ammonia are produced;

(n) recycling the first liquid phase containing ammonium carbamate as per steps (d) and (e); and (o) mixing the second liquid phase essentially consisting of substantially pure ammonia with the feed ammonia of step (a), preheating the total ammonia in the preceding low pressure condensation step (l) and feeding the resulting preheated ammonia to the synthesis reactor of step (a) through a liquid/liquid ejector for recycling the ammonium carbamate, in which the liquid ammonia acts as the drive fluid.

* * * * *

UNITED STATES PATENT AND TRADEMARK OFFICE
CERTIFICATE OF CORRECTION

PATENT NO. : 5,849,952
DATED : December 8, 1998
INVENTOR(S) : Giuseppe Carloni and Franco Granelli It is certified that error appears in the above-identified patent and that said Letters Patent is hereby corrected as shown below:

On the title page, Item [73] please change the spelling of the Assignee's name from "shamprogetti S.p.A. " to —Snamprogetti S.p.A. —.

Also on the title page, item [30] please change the Foreign Application Priority Data from "Feb. 19,1992 [JP] Japan 4-032308" to —Sept. 15,1989 Italy - 21741 A/89 —.

Signed and Sealed this

First Day of June, 1999

Attest:

Q. TODD DICKINSON

*Attesting Officer*        *Acting Commissioner of Patents and Trademarks*